United States Patent
de Melis et al.

(10) Patent No.: US 9,808,164 B2
(45) Date of Patent: Nov. 7, 2017

(54) EVALUATION OF CARDIAC DYSSYNCHRONY BASED ON CHEST WALL MOTION AND ELECTRICAL CARDIAC ACTIVITY

(75) Inventors: Mirko de Melis, Maastricht (NL); Giorgio Corbucci, Cento (IT)

(73) Assignee: Medtronic, Inc., Minneapolis, MN (US)

(*) Notice: Subject to any disclaimer, the term of this patent is extended or adjusted under 35 U.S.C. 154(b) by 1294 days.

(21) Appl. No.: 13/596,833

(22) Filed: Aug. 28, 2012

(65) Prior Publication Data
US 2013/0085404 A1 Apr. 4, 2013

Related U.S. Application Data

(60) Provisional application No. 61/541,505, filed on Sep. 30, 2011.

(51) Int. Cl.
*A61B 5/0245* (2006.01)
*A61B 5/0452* (2006.01)
*A61B 5/11* (2006.01)

(52) U.S. Cl.
CPC .......... *A61B 5/0245* (2013.01); *A61B 5/0452* (2013.01); *A61B 5/1102* (2013.01); *A61B 2562/0219* (2013.01)

(58) Field of Classification Search
CPC .......... A61B 5/02; A61B 5/0452; A61N 1/365
USPC .......................................... 600/513; 607/18
See application file for complete search history.

(56) References Cited

U.S. PATENT DOCUMENTS

| | | | |
|---|---|---|---|
| 7,610,088 B2 | 10/2009 | Chinchoy | |
| 2006/0095085 A1* | 5/2006 | Marcus | A61B 5/1107 607/17 |
| 2008/0021336 A1* | 1/2008 | Dobak | A61B 5/021 600/508 |
| 2008/0114256 A1* | 5/2008 | Zhang | A61B 5/11 600/488 |

(Continued)

OTHER PUBLICATIONS

De Melis et al., "A Noncontact Approach for the Evaluation of Large Artery Stiffness: A Preliminary Study," American Journal of Hypertension, Ltd., Dec. 2008;21(12):1280-3. Epub Sep. 11, 2008. (4 pp.).

(Continued)

*Primary Examiner* — Christopher D Koharski
*Assistant Examiner* — Roland Dinga

(57) ABSTRACT

Cardiac dyssynchrony of a patient may be evaluated based on electrical activity of a heart of the patient and corresponding chest wall motion of the patient sensed via an external accelerometer. In one example, an acceleration signal indicative of the chest wall motion is generated by an external accelerometer positioned on the chest wall of the patient. A processor of a diagnostic device integrates the acceleration signal to generate a velocity signal and temporally correlates the velocity signal and an electrical cardiac signal. The processor determines a time delay between a deflection of the electrical cardiac signal indicating ventricular electrical activation and a subsequent greatest peak of the velocity signal. The time delay may indicate a degree of electromechanical delay of the left ventricle. In some examples, the processor generates an output indicative of a cardiac dyssynchrony status based on the time delay.

30 Claims, 4 Drawing Sheets

(56) References Cited

U.S. PATENT DOCUMENTS

2009/0030471 A1    1/2009    Rousso et al.
2010/0056907 A1    3/2010    Rappaport et al.

OTHER PUBLICATIONS

De Melis et al,. "Identification of cardiac events by Optical Vibrocardiograpy: comparison with Phonocardiography," Engineering in Medicine and Biology Society, 29th Annual International Conference of the IEEE, 2007;2007:2956-2959 (4 pp.).

Halvorsen et al., "Feasibility of a three-axis epicardial accelerometer in detecting myocardial ischemia in cardiac surgical patients," J Thorac Cardiovasc Surg Dec. 2008;136:1496-1502.

Baquero et al., "Cardiac resynchronization therapy: evaluation of ventricular dysynchrony and patient selection," Arch Cardiol Mex 2010;80(4):289-300.

Morbiducci et al., "Optical Vibrocardiography: A Novel Tool for the Optical Monitoring of Cardiac Activity," Annals of Biomedical Engineering, Jan. 2007, 35(1):45-58 (14 pp.).

Korzeniowska-Kubacka et al., "Usefulness of Seismocardiography for the Diagnosis of Ischemia in Patients with Coronary Artery Disease," A.N.E. Jul. 2005;10(3):281-287.

Aubert et al., "Laser Method for Recording Displacement of the Heart and Chest Wall," J Biomed Eng. Apr. 1984; 6(2):134-40.

Nelson et al., "Predictors of Systolic Augmentation From Left Ventricular Preexcitation in Patients With Dilated Cardiomyopathy and Intraventricular Conduction Delay," Circulation Jun. 13, 2000;101:2703-2709.

Penicka et al., "Improvement of Left Ventricular Function After Cardiac Resynchronization Therapy is Predicted by Tissue Doppler Imaging Echocardiography," Circulation Mar. 2, 2004;109:978-983.

Cleland et al., "The Effect of Cardiac Resynchronization on Morbidity and Mortality in Heart Failure," N Engl J Med Apr. 2005;352:1539-1549.

Richardson et al., "Predictors and treatment response with cardiac resynchronization therapy in patients with heart failure characterized by dyssynchrony: a pre-defined analysis from the CARE-HF trial," Eur Heart J Aug. 2007; 28:1827-1834, Epub May 31, 2007.

\* cited by examiner

EVALUATION OF CARDIAC DYSSYNCHRONY BASED ON CHEST WALL MOTION AND ELECTRICAL CARDIAC ACTIVITY

This application claims the benefit of U.S. Provisional Application No. 61/541,505, entitled, "EVALUATION OF CARDIAC DYSSYNCHRONY BASED ON CHEST WALL MOTION AND ELECTRICAL CARDIAC ACTIVITY," and filed on Sep. 30, 2011, the entire content of which is incorporated herein by reference.

TECHNICAL FIELD

The disclosure relates to patient diagnostics.

BACKGROUND

In some cases, patients with heart failure are treated with cardiac resynchronization therapy (CRT), which is a form of cardiac pacing. In some examples, CRT involves delivery of pacing pulses to both ventricles ("biventricular pacing") to synchronize their contraction. In other examples, CRT involves delivery of pacing pulses to one ventricle to synchronize its contraction with that of the other ventricular, such as pacing the left ventricle to synchronize its contraction with that of the right ventricle.

SUMMARY

In general, the disclosure is directed to assessing cardiac dyssynchrony of a patient based on an evaluation of electrical activity of a heart of the patient and corresponding chest wall motion of the patient sensed via an external accelerometer. The disclosure describes methods for assessing cardiac dyssynchrony of the patient and various devices and systems configured to assess cardiac dyssynchrony of the patient. In one example, an electrical cardiac signal that indicates electrical activity of the heart of the patient is sensed, along with chest wall motion of the patient (e.g., via an external accelerometer positioned on a chest wall of the patient), from which a signal indicative of the velocity of the chest wall motion can be generated. The velocity signal and the electrical cardiac signal are temporally correlated, and a time delay between a deflection of the electrical cardiac signal indicating ventricular electrical activation and a subsequent greatest peak (e.g., a greatest absolute amplitude of the velocity signal) of the velocity signal is determined. The time delay may indicate a degree of electromechanical delay of the later contracting ventricle.

In some examples, the time delay can be compared to one or more thresholds to assess the cardiac dyssynchrony status of the patient, e.g., to categorize the patient's cardiac dyssynchrony. In addition, in some examples, a type of pacing therapy for the patient can be selected based on the time delay, or one or more parameters of a patient's pacing therapy can be modified based on the time delay.

In one example, the disclosure is directed to a system comprising an external accelerometer configured to generate an acceleration signal indicative of chest wall motion of a patient, and a processor configured to integrate the acceleration signal to generate a velocity signal, receive an electrical cardiac signal indicative of electrical cardiac activity of the patient, temporally correlate the velocity signal with the electrical cardiac signal, determine a time delay between a deflection of the electrical cardiac signal indicative of electrical activation of a ventricle of a heart of the patient and a subsequent greatest peak of the velocity signal, and generate an output indicative of a cardiac dyssynchrony status of the patient based on the time delay. In some examples, the system comprises a sensing module configured to generate the electrical cardiac signal.

In another example, the disclosure is directed to a method comprising, with a processor, receiving, from an external accelerometer, an acceleration signal indicative of chest wall motion of the patient, wherein the external accelerometer generates the acceleration signal while the external accelerometer was positioned on a chest wall of a patient;. The method further comprises, with the processor, integrating the acceleration signal to generate a velocity signal and, with the processor, receiving an electrical cardiac signal of a patient indicative of electrical cardiac activity of the patient. The method further comprises, with the processor, temporally correlating the velocity signal with the electrical cardiac signal, determining a time delay between a deflection of the electrical cardiac signal indicative of electrical activation of a ventricle of a heart of the patient and a subsequent greatest peak of the velocity signal, and generating an output indicative of a cardiac dyssynchrony status of the patient based on the time delay.

In another example, the disclosure is directed to a system comprising means for generating an acceleration signal indicative of chest wall motion of a patient from a location external to the patient, means for integrating the acceleration signal to generate a velocity signal, means for temporally correlating the velocity signal with an electrical cardiac signal indicative of electrical cardiac activity of the patient, means for determining a time delay between a deflection of the electrical cardiac signal indicative of electrical activation of a ventricle of a heart of the patient and a subsequent greatest peak of the velocity signal, and means for generating an output indicative of a cardiac dyssynchrony status of the patient based on the time delay.

In another example, the disclosure is directed to a method comprising positioning an accelerometer on an external surface of a chest wall of a patient, wherein the accelerometer is configured to generate an acceleration signal indicative of chest wall motion of a patient, and, with a diagnostic device, generating an output indicative of a cardiac dyssynchrony status of the patient, wherein the diagnostic device is configured to integrate the acceleration signal to generate a velocity signal, temporally correlate the velocity signal with an electrical cardiac signal indicative of electrical cardiac activity of the patient, determine a time delay between a deflection of the electrical cardiac signal indicative of electrical activation of a ventricle of a heart of the patient and a subsequent greatest peak of the velocity signal, and generate the output indicative of a cardiac dyssynchrony status of the patient based on the time delay.

In another example, the disclosure is directed to a computer-readable medium containing instructions. The instructions, when executed by a processor, cause the processor to receive, from an external accelerometer, an acceleration signal indicative of chest wall motion of the patient, wherein the external accelerometer generates the acceleration signal while the external accelerometer was positioned on a chest wall of a patient, integrate the acceleration signal to generate a velocity signal, receive an electrical cardiac signal of a patient indicative of electrical cardiac activity of the patient, temporally correlate the velocity signal with the electrical cardiac signal, determine a time delay between a deflection of the electrical cardiac signal indicative of electrical activation of a ventricle of a heart of the patient and a subsequent greatest peak of the velocity signal, and generate an output indicative of a cardiac dyssynchrony status of the patient based on the time delay.

In another aspect, the disclosure is directed to a computer-readable storage medium, which may be an article of manufacture. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable mediums described herein are non-transitory.

The details of one or more examples are set forth in the accompanying drawings and the description below. Other features, objects, and advantages will be apparent from the description and drawings, and from the claims.

DETAILED DESCRIPTION

Figure 1:
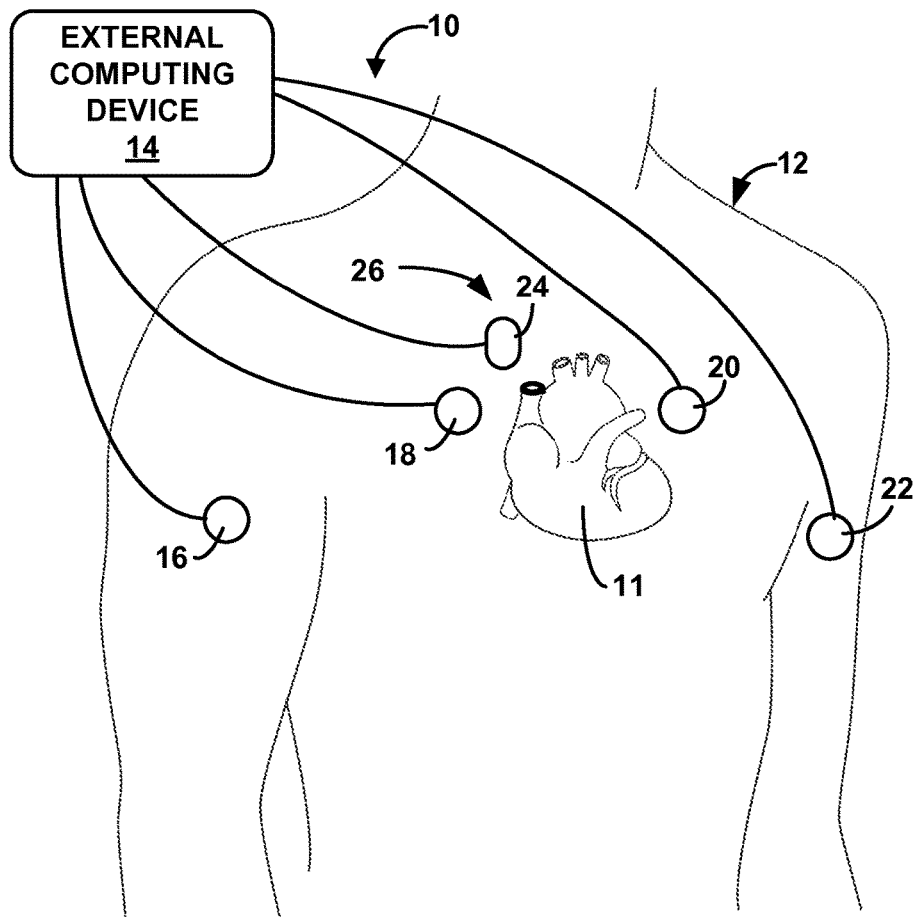
FIG. 1 is a conceptual diagram illustrating an example system that may be used to assess cardiac dyssynchrony of a heart of a patient, where the system includes an external diagnostic device electrically connected to electrodes and an external accelerometer.

Some cardiac conditions, such as heart failure and/or left bundle branch block (LBBB), may be associated with dyssynchrony of mechanical contraction of the heart, which may also be referred to as ventricular dyssynchrony. Intraventricular dyssynchrony may be characterized by the relative delay of contraction among different segments of a single ventricle (e.g., a left ventricle or a right ventricle) of a heart of a patient. Interventricular dyssynchrony may be characterized by left and right ventricles of the heart that do not contract in synchrony (e.g., simultaneously or near simultaneously). In some patients with interventricular or intraventricular dyssynchrony, the left ventricle contracts slower and later following contraction of the right ventricle compared to a healthy heart. Accordingly, the delay of left ventricular contraction relative to the electrical activation of the right ventricle (which generally represents the timing of right ventricular contraction) can be a marker indicative of the extent of a patient's cardiac interventricular or intraventricular dyssynchrony.

As described in further detail below, a time delay between electrical activation of the right ventricle and contraction of the later-contracting ventricle is used to determine a cardiac dyssynchrony status of a patient. The cardiac dyssynchrony status may indicate the extent of the cardiac dyssynchrony of a patient, e.g., relative to a healthy patient with little to no ventricular dyssynchrony (e.g., ventricular dyssynchrony that does not merit the delivery of electrical cardiac rhythm management therapy). In some examples, a computing device provides an output indicative of an automatically determined cardiac dyssynchrony status (e.g., independently determined by the computing device without user input indicating the cardiac dyssynchrony status). In addition, in some examples, a computing device automatically selects a type of pacing therapy for a patient based on the determined cardiac dyssynchrony status of the patient or automatically adjusts one or more parameters of pacing therapy delivered to the patient.

As described in further detail below, in some examples, an external computing device is configured to generate an indication of the cardiac dyssynchrony status of a patient based on electrical cardiac activity of the patient and chest wall motion of the patient sensed by an external accelerometer. The external accelerometer is configured to generate an acceleration signal that, when integrated, provides a velocity signal that is indicative of the timing of the mechanical contraction of the later-contracting ventricle. The electrical cardiac activity can indicate the timing of the electrical activation of the right ventricle, which may correspond to the contraction of the right ventricle in some patients. In some examples, the electrical cardiac activity is indicated by an electrocardiogram (ECG) or an electrogram (EGM). The electrical cardiac activity that indicates electrical ventricular activation may be a deflection of the ECG or EGM, such as, for example, a Q-wave or an R-wave of the ECG or EGM.

Instead of, or in addition to, the electrical cardiac signal, the electrical cardiac activity that indicates electrical ventricular activation is indicated by information received from a cardiac rhythm management device (e.g., an electrical stimulator, also referred to herein as a cardiac stimulator) that is configured to deliver pacing pulses to the patient. The electrical cardiac activity that indicates electrical ventricular activation may be, for example, the timing of a pacing pulse delivered by the cardiac rhythm management device. While an electrical cardiac signal is primarily referred to below, in other examples, other types of activity indicative of electrical cardiac activity of a patient may be used to assess cardiac dyssynchrony of a patient.

A time delay between the right ventricular activation (e.g., a pacing pulse or a predetermined deflection of the electrical cardiac signal, such as a Q-wave or R-wave of the ECG or EGM) and a subsequent greatest peak of the velocity signal can be determined. In some examples, the determined time delay indicates the electromechanical delay of the left ventricle contraction, e.g., relative to the electrical activation of the right ventricle. The greatest peak referred to herein may be a greatest absolute velocity, which may be a lowest velocity value (e.g., a trough of the velocity signal) or a highest velocity value. In some examples, the greatest peak of the velocity signal is the greatest peak observed after the beginning of the right ventricular activation, and may be, for example, the greatest velocity peak observed during a time period between the Q-wave and a subsequent P-wave or within a time period of about 400 milliseconds (ms) that begins at the Q-wave.

As described in further detail below, in some examples, an external computing device is configured to generate an indication of the cardiac dyssynchrony status of a patient based on based on electrical cardiac activity of the patient and chest wall motion of the patient sensed by an external accelerometer. An external device that is configured to provide an indication of the extent of a patient's cardiac dyssynchrony with noninvasive (e.g., non-implanted and external) sensors provides a noninvasive diagnostic tool that a clinician can use in order to formulate a therapy regimen for a patient (e.g., select a new therapy regimen or modify an existing therapy regimen). Evaluating the extent of the patient's cardiac dyssynchrony with an external device may be useful for determining whether the patient would benefit from cardiac rhythm management therapy (also referred to herein as "cardiac rhythm therapy") prior to implanting a cardiac rhythm therapy device in the patient.

In addition, evaluating the extent of the patient's cardiac dyssynchrony with an external device may be useful for selecting a type of cardiac rhythm management therapy for a particular patient, such as a type of cardiac resynchronization therapy (CRT), prior to implanting a cardiac rhythm management (e.g., a pacemaker) in the patient. It is believed that mechanical dyssynchrony is a useful predictor for CRT efficacy, such that reliable identification of cardiac dyssynchrony prior to implanting a cardiac rhythm management device in the patient may be increase the success of CRT. Moreover, because some types of CRT are aimed at resynchronizing the left ventricular wall contraction with the right ventricular wall contraction, thereby decreasing the delay of the greatest velocity peak of a velocity signal indicative of chest wall motion relative to the electrical cardiac signal deflection indicative of electrical activation of the right ventricle, the time delay between the greatest velocity peak and the R-wave of the sinus rhythm may provide an indication of the effectiveness of CRT for a particular patient.

If a cardiac rhythm management therapy device is already implanted in the patient, evaluating the extent of the patient's cardiac dyssynchrony (post-implant of the device) with an external device using the techniques described herein may be useful for noninvasively determining whether the cardiac rhythm therapy device is efficacious, or whether one or more parameters of the device need to be modified. For example, if the time delay between the greatest velocity peak and a sensed Q-wave of the electrical cardiac signal is greater than a predetermined threshold, a diagnostic device or clinician may adjust the pacing intervals of the cardiac rhythm therapy device in order to reduce the time delay.

In one proposed technique for assessing cardiac dyssynchrony, heart sounds are sensed (e.g., sensed by an acoustic sensor) in order to detect the left ventricular wall contraction, and a time delay between the determined left ventricular wall contraction and a right ventricular wall contraction is determined based on the heart sounds. While this technique may be useful, in some cases, the time delay between the left ventricular wall contraction and the right ventricular wall contraction may not be accurately determinable through heart sounds because the heart sounds can be relatively low and dispersed in some patients with heart failure. In contrast to detecting left ventricular wall contraction based heart sounds, the external devices described herein are configured to detect left ventricular wall contraction based on a signal generated by an accelerometer, and, in particular, a velocity signal generated by integrating the acceleration signal generated by the accelerometer. The velocity signal may be indicative of the motion of the heart of the patient attributable to ventricular contraction. The velocity signal may, in some examples, be a more robust parameter for detecting left ventricular contraction compared to heart sounds, e.g., may be less prone to signal noise.

In another technique that has been proposed for assessing cardiac dyssynchrony, tissue Doppler is used to identify the time of maximum displacement of ventricular walls. While this may be useful in some examples, the tissue Doppler technique can be more computationally intensive than the techniques for evaluating cardiac dyssynchrony described herein, where the computational intensity may increase the cost of a system for assessing the extent of cardiac dyssynchrony of a patient. In addition, the tissue Doppler technique for assessing cardiac dyssynchrony may have more variability between successive measurements compared to the accelerometer-based sensing for assessing cardiac dyssynchrony described herein.

FIG. 1 is a conceptual diagram illustrating an example system 10 that may be used to diagnose cardiac dyssynchrony of heart 11 of patient 12. System 10 includes external diagnostic device 14, which is electrically connected to electrodes 16, 18, 20, 22, and accelerometer 24.

External diagnostic device 14 is configured to sense electrical cardiac activity of patient 14 via electrodes 16, 18, 20, 22. For example, diagnostic device 14 may include a sensing module that is configured to generate an ECG based on signals from electrodes 16, 18, 20, 22. While four electrodes 16, 18, 20, 22 are shown in FIG. 1, in other examples, system 10 can include any suitable number of electrodes with which diagnostic device 14 senses electrical cardiac activity of patient 12. For example, system 10 may include ten electrodes and diagnostic device 14 may generate an ECG using a 12-lead ECG technique.

In some cases, electrodes 16, 18, 20, 22 may be secured to patient 12 in order to improve the sensitivity of the electrodes to electrical cardiac activity of heart 11 of patient 12. In these examples, electrodes 16, 18, 20, 22 can be attached to patient 12 using any suitable mechanism, such as using an adhesive or a belt. In addition, in some examples, a conductive gel is positioned between one or more of the electrodes 16, 18, 20, 22 and the epidermis of patient 12 to improve the sensitivity of the electrodes to electrical cardiac activity of the patient.

In the example shown in FIG. 1, diagnostic device 14 is electrically connected to electrodes 16, 18, 20, 22 and accelerometer 24 via a wired connection and receives signals generated by accelerometer 24 via the wired connection. In other examples, diagnostic device 14 can be physically separate (e.g., not physically connected) from electrodes 16, 18, 20, 22 and accelerometer 24 and wirelessly communicate with (e.g., send signals to and receive signals from) electrodes 16, 18 and accelerometer 24. For example, electrodes 16, 18, 20, 22 can be a part of an ECG sensing module that is physically separate from diagnostic device 14 and includes a telemetry module configured to wirelessly communicate with diagnostic device 14. Similarly, accelerometer 24 can be a part of a sensing module physically separate from diagnostic device 14, and, in some cases, electrodes 16, 18, 20, 22, where the sensing module includes a telemetry module configured to wirelessly communicate with diagnostic device 14.

In other examples, instead of or in addition to a sensing module within diagnostic device 14 that generates the ECG with, e.g., electrodes 16, 18, 20, 22, diagnostic device 14 may be configured to communicate with a physically separate sensing device that transmits an electrical cardiac signal to diagnostic device 14. For example, diagnostic device 14 may be configured to communicate wirelessly or via a wired connection with a physically separate patient monitor that generates the ECG based on sensed electrical cardiac activity. In yet another example, diagnostic device 14 may be configured to communicate with an implantable sensing device that is configured to generate an EGM, which indicates the electrical activity of heart 11 of patient 12. The patient monitor may be a dedicated ECG monitor or may sense one or more additional patient parameters, such as blood oxygen saturation. As another example, an implantable sensing device may be implanted in patient 12 and may wirelessly communicate with diagnostic device 14 to transmit the EGM to diagnostic device 14. Any combination of the sensing devices described above may also be used together. While an external electrical cardiac signal monitor and ECG are primarily referred to below, in other examples, diagnostic device 14 may perform any of the techniques and provide an output indicative of a cardiac dyssynchrony status of a patient based on an EGM instead of, or in addition to, an ECG.

Accelerometer 24 may be any suitable accelerometer configured to generate a signal that changes as a function of mechanical cardiac activity of patient 12. Accelerometer may be, for example, a single-axis accelerometer, a two-axis accelerometer, or a three-axis accelerometer, or may be comprised of two or more single-axis or multi-axis accelerometers arranged to detect acceleration in respective axes. When placed on chest wall 26 of patient 12, as shown in FIG. 1, accelerometer 24 generates a signal indicative of acceleration of chest wall 26 of patient 12, which is at least partially caused by mechanical cardiac activity (e.g., mechanical contraction of heart 11) of patient 12. In some examples, chest wall 26 is located in the thorax region of patient 12. In some examples, accelerometer 24 may be positioned on chest wall 26 of patient 12 and aligned with heart 11 (e.g., aligned in the dorsoventral direction). In other examples, accelerometer 24 may be positioned to be on chest wall 26 anywhere in the thorax region of patient 12. Accelerometer 24 may be positioned on chest wall 26 to gather the acceleration information while patient 12 is in any suitable posture, which can be selected by a clinician. In some examples, patient 12 is in a supine position when accelerometer 24 generates a signal that changes as a function of mechanical cardiac activity of patient 12.

When accelerometer 24 is placed on an exterior surface of chest wall 26 of patient 12, either directly on the epidermis of patient 12 or indirectly (e.g., clothing or another material may be positioned between accelerometer 24 and the epidermis of patient 12), accelerometer 24 moves as chest wall 26 moves. As accelerometer 24 moves, accelerometer 24 generates a signal indicative of acceleration in one or more directions, which, in the example shown in FIG. 1, includes a direction in which chest wall 26 moves when right and left ventricles of heart 11 of patient 12 contract.

In some examples, accelerometer 24 is configured to be a single axis accelerometer, and is positioned on chest wall 26 of patient such that the axis is aligned with the anteroposterior direction (a direction from a head to toes of patient 12). In some other examples, accelerometer 24 is configured to be a multi-axis accelerometer and is positioned on chest wall 26 of patient such that one axis is aligned with the anteroposterior direction. In some cases, a clinician only aligns one axis of accelerometer 24 in a particular direction. In other cases, however, the clinician may align more than one axis of accelerometer 24 (if accelerometer 24 is a multi-axis accelerometer) in a particular direction relative to heart 11 of patient 12. Another axis of the multi-axis accelerometer may be, for example, aligned with the dorsoventral direction (a direction from a spinal column to belly of patient 12).

An external surface of accelerometer 24 may include one or more visible or otherwise detectable (e.g., palpable) markings that indicates the axis or axes in which accelerometer 24 is configured to sense acceleration. The markers may help a clinician properly position accelerometer 24 on chest wall 26 of patient 12 to sense the acceleration of chest wall 26 that results when ventricles of patient 12 contract.

Accelerometer 24 may be positioned on chest wall 26 at any suitable location that results in an accelerometer signal that indicates acceleration of chest wall 26 attributable to mechanical activity of heart 11 of patient 12 (e.g., from the pumping function of the cardiac muscle). Accelerometer 24 may be positioned externally to patient 12 and on a portion of chest wall 26 proximate enough to heart 11 such that the portion of chest wall 26 moves as heart 11 contracts may generate a signal indicative of global motion of heart 11, e.g., motion of both ventricles of heart 11. This is in contrast to some accelerometers implanted within heart 11, which may only generate a signal indicative of motion of one portion of heart 11 near which the accelerometer is implanted. It is believed that the signal indicative of global motion of heart 11 may still provide an indication of the timing of ventricular contraction that is useful for evaluating the extent of cardiac dyssynchrony of patient 12.

In some examples, accelerometer 24 can be attached to patient 12 in order to reduce any relative motion between accelerometer and patient 12, such that motion of accelerometer 24 more accurately and precisely reflects motion of chest wall 26 of patient 12. In these examples, accelerometer 24 can be attached to patient 12 using any suitable technique, such as using an adhesive, via a mechanical strap, or the like.

In order to detect the contraction of the later-contracting ventricular based on the signal generated by accelerometer 24, diagnostic device 14 may determine a velocity signal based on the acceleration signal generated by accelerometer 24. For example, diagnostic device 14 may receive the accelerometer signal from accelerometer 24 and integrate the signal to generate a velocity signal. The integration of the accelerometer signal may remove components of the acceleration attributable to vibration of chest wall 26 from closing of valves of heart 11. A greatest peak of the velocity signal may correspond to the time at of the left ventricular contraction.

Diagnostic device 14 is an external computing device (i.e., is not implanted in patient 14) that is configured to receive signals from electrodes 16, 18, 20, 22 and accelerometer 24 and generate an output indicative of a cardiac dyssynchrony status of patient 12. Diagnostic device 14 may comprise a handheld computing device, computer workstation, or networked computing device. As described in further detail with respect to FIG. 2, diagnostic device 14 may include a user interface that presents information to and receives input from a user. The information presented to a user may be, for example, a graphical or alphanumeric indication of the cardiac dyssynchrony status of patient 12.

In some examples, a user may interact with diagnostic device 14 remotely via a networked computing device.

Figure 2:
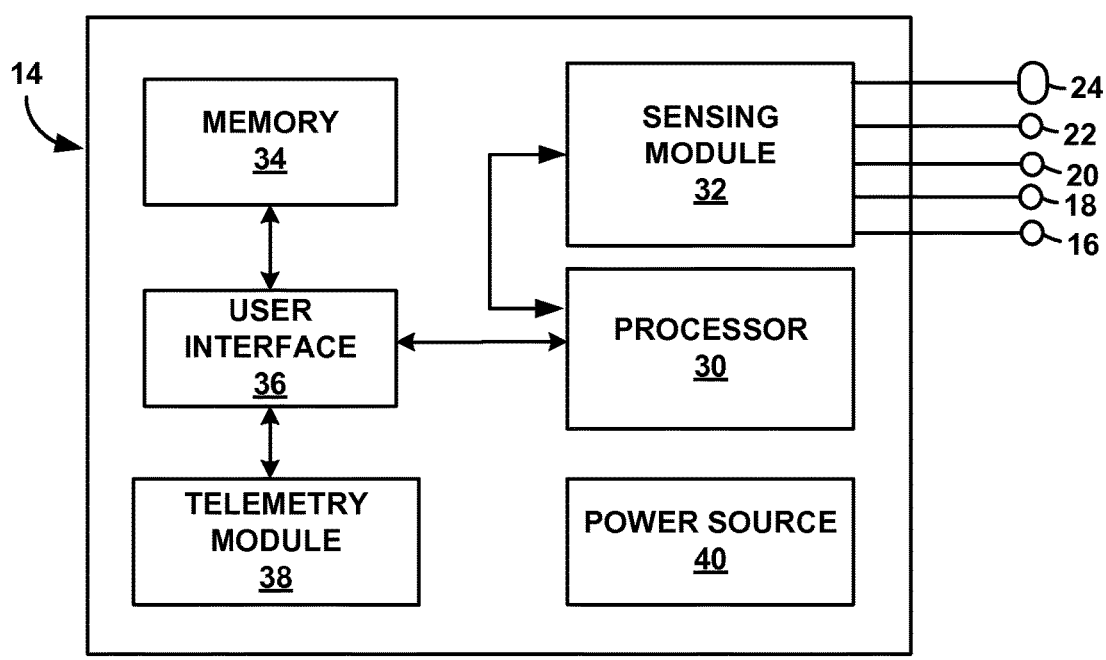
FIG. 2 is a functional block diagram of an example configuration of the diagnostic device of the system shown in FIG. 1.

FIG. 2 is a functional block diagram of an example configuration of diagnostic device 14. As shown in FIG. 2, diagnostic device 14 includes processor 30, sensing module 32, memory 34, user interface 36, telemetry module 38, and power source 40. Diagnostic device 14 may be a dedicated hardware device with dedicated software for generating an output indicative of a cardiac dyssynchrony status of patient 12 and determining the cardiac dyssynchrony status based on sensed electrical cardiac activity and a signal generated by accelerometer 24. In other examples, diagnostic device 14 may be an off-the-shelf computing device running an application that enables diagnostic device 14 to receive signals from electrodes 16, 18, 20, 22 and accelerometer 24 and generate an output indicative of a cardiac dyssynchrony status of patient. In some examples, diagnostic device 14 is also a medical device programmer, which is a device that is configured to program a medical device, such as an implantable or external cardiac rhythm management device.

Processor 30 can take the form any one or more of a microprocessor, a controller, a digital signal processor (DSP), an application specific integrated circuit (ASIC), a field-programmable gate array (FPGA), or equivalent discrete or integrated logic circuitry. In some examples, processor 30 may include multiple components, such as any combination of one or more microprocessors, one or more controllers, one or more DSPs, one or more ASICs, or one or more FPGAs, as well as other discrete or integrated logic circuitry. The functions attributed to processor 30 herein, as well as other processors referred to herein, may be embodied as software, firmware, hardware or any combination thereof.

Sensing module 32 is configured to generate a signal indicative of electrical activity of heart 11 of patient 12, e.g., based on signals sensed via electrodes 16, 18, 20, 22 in the example shown in FIG. 2. For example, sensing module 32 may be configured to (e.g., may include circuitry) generate an ECG based on signals sensed via electrodes 16, 18, 20, 22. In addition, in the example shown in FIG. 2, sensing module 32 is configured to receive a signal generated by accelerometer 24, e.g., via a wired or wireless connection between accelerometer 24 and sensing module 32.

Memory 34 may store instructions that cause processor 30 to provide the functionality ascribed to diagnostic device 14 herein, and information used by processor 30 to provide the functionality ascribed to diagnostic device 14 herein. In addition, memory 34 may be configured to store cardiac dyssynchrony statuses generated by processor 30, electrical cardiac signals generated by sensing module 32, signals generated by accelerometer 24, threshold values (e.g., threshold time delay values) used by processor 30 to generate cardiac dyssynchrony statuses, including those discussed in this disclosure, and any other suitable information.

Memory 34 may include any fixed or removable magnetic, optical, or electrical media, such as RAM, ROM, CD-ROM, hard or floppy magnetic disks, EEPROM, or the like. Memory 34 may also include a removable memory portion that may be used to provide memory updates or increases in memory capacities. A removable memory may also allow patient data to be easily transferred to another computing device, or to be removed before diagnostic device 14 is used to diagnose the cardiac dyssynchrony of another patient.

A clinician may interact with diagnostic device 14 via user interface 36, which may include a display to present a graphical user interface to a user, and a keypad or another mechanism for receiving input from a user. The display may be, for example, a liquid crystal display (LCD), light-emitting diode (LED) display, an organic LED, or any other suitable display. The mechanism for receiving input form a user can include buttons, a keypad, and/or one or more other input devices, such as a mouse, trackball, or stylus. In some examples, the display may be a touch screen that enables the user to provide input by directly interacting with the display screen.

In some examples, diagnostic device 14 may communicate with another device, such as an implantable medical device or another external computing device. This communication is possible through the use of telemetry module 38, which may be coupled to an internal antenna or an external antenna. Telemetry module 38 may be configured to communicate with another computing device via wireless communication techniques, or direct communication through a wired connection. Examples of local wireless communication techniques that may be employed to facilitate communication between diagnostic device 14 and another computing device include RF communication according to the 802.11 or Bluetooth specification sets, infrared communication, e.g., according to the IrDA standard, or other standard or proprietary telemetry protocols. In this manner, other external devices may be capable of communicating with diagnostic device 14 without needing to establish a secure wireless connection. An additional computing device in communication with diagnostic device 14 may be a networked device such as a server capable of processing information retrieved from diagnostic device 14.

Figure 3:
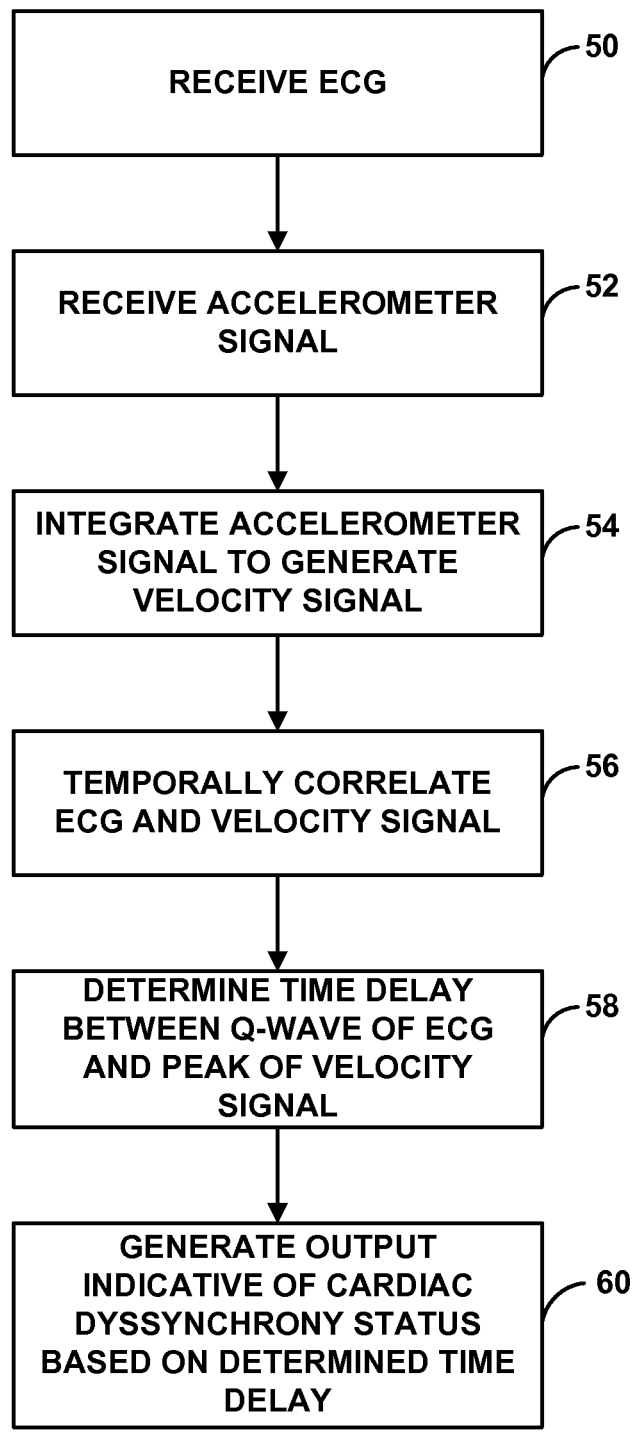
FIG. 3 is a flow diagram illustrating an example technique for determining a cardiac dyssynchrony status of a patient based on an electrical cardiac signal and a signal indicative of velocity of a chest wall of a patient.
Figure 4A:
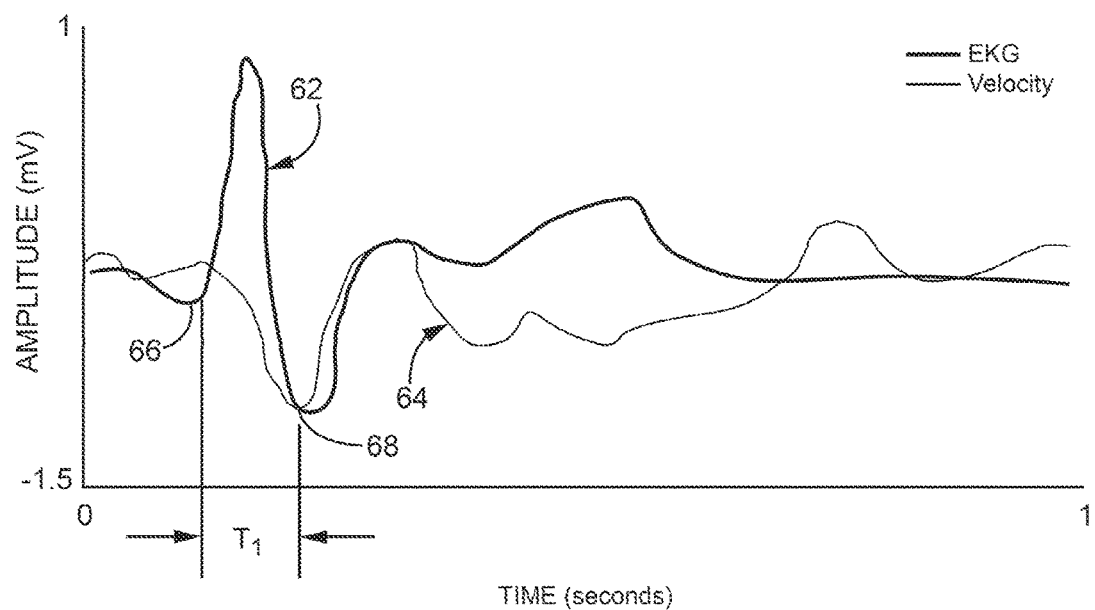
FIG. 4A is an example graphical representation of an electrocardiogram signal of a patient that does not exhibit ventricular dyssynchrony that merits cardiac rhythm management therapy delivered by a medical device, and a temporally correlated velocity signal that indicates the velocity of the chest wall of the patient.
Figure 4B:
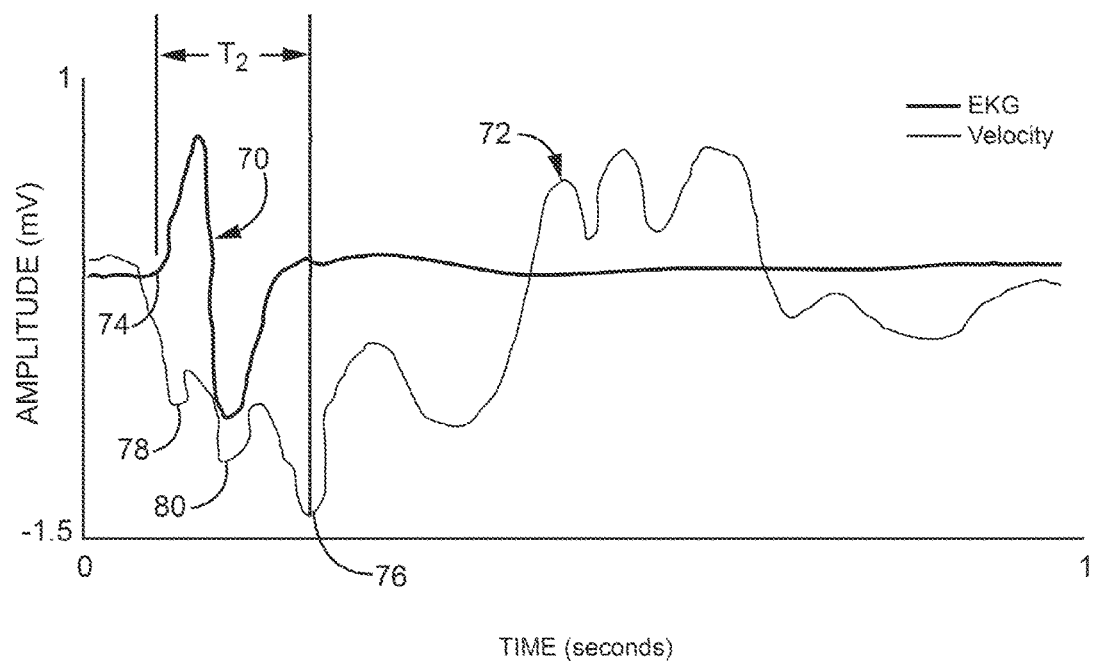
FIG. 4B is an example graphical representation of an electrocardiogram signal of a patient that exhibits ventricular dyssynchrony and a temporally correlated velocity signal that indicates the velocity of the chest wall of the patient.
Figure 5:
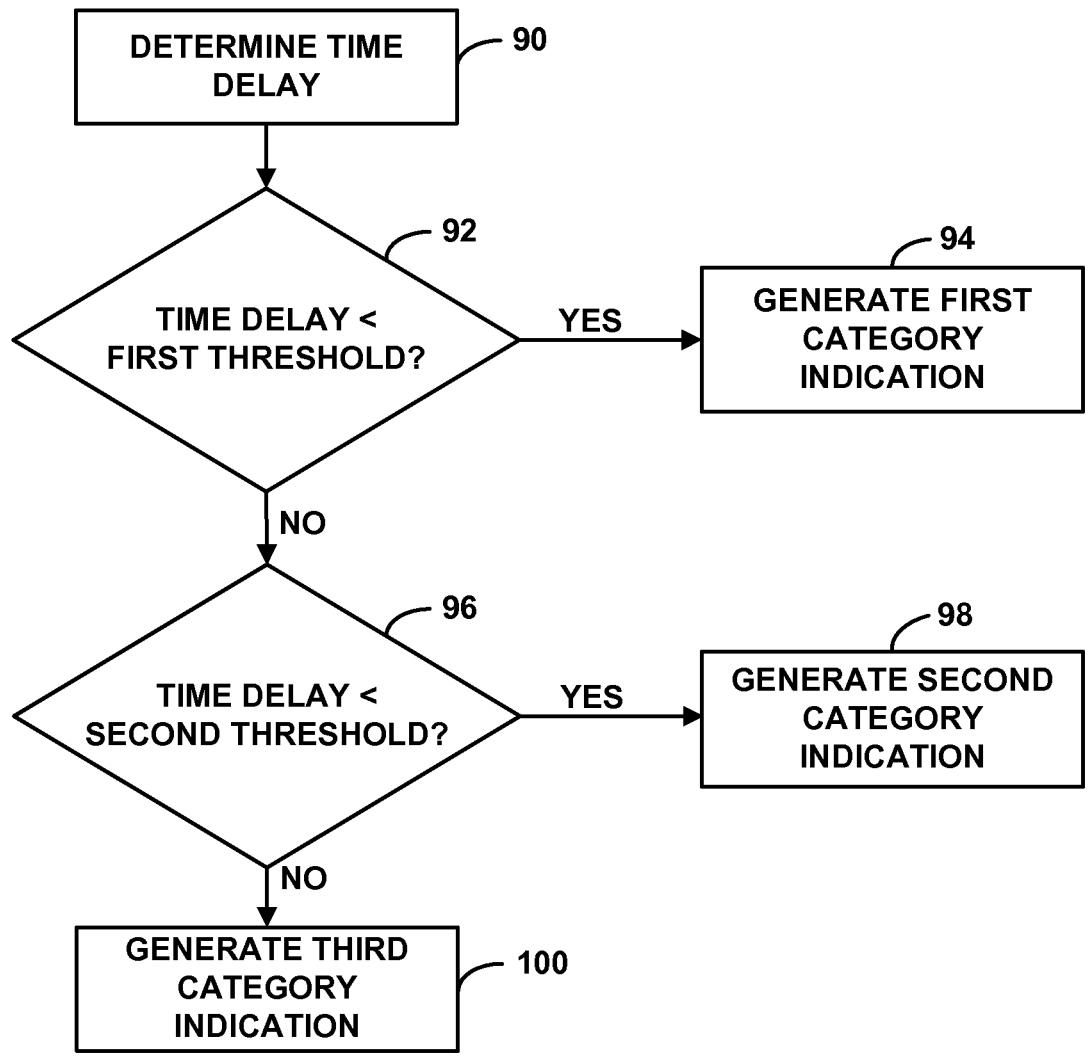
FIG. 5 is a flow diagram of an example technique for determining a cardiac dyssynchrony status of a patient based on time delay between a deflection of an electrical cardiac signal indicative of ventricular electrical activation of the patient and a subsequent greatest peak of a velocity signal that indicates the velocity of the chest wall of the patient.

Power source 40 is configured to deliver operating power to the components of diagnostic device 14. Power source 40 may include a battery and a power generation circuit to produce the operating power. The battery may be a rechargeable or non-rechargeable battery FIG. 3 is a flow diagram illustrating an example technique for determining a cardiac dyssynchrony status of a patient based on an electrical cardiac signal and a signal indicative of velocity of chest wall 26 of patient 12. While FIG. 3, as well as FIG. 5, is described with respect to processor 30 of diagnostic device 14, in other examples, all or part of the technique shown in FIGS. 3 and 4 may be performed by another device, such as another computing device.

According to the technique shown in FIG. 3, processor 30 receives an ECG (or another suitable electrical cardiac signal) from sensing module 32, which generates the ECG based on signals sensed by electrodes 16, 18, 20, 22 (FIG. 1) (50). In addition, processor 30 receives an accelerometer signal from external accelerometer 24, either wirelessly or via a wired connection (as shown in FIG. 1) (52). The accelerometer signal is indicative of acceleration of chest wall 26 of patient 12 proximate to heart 11, such that the acceleration of chest wall 26 is at least partially attributable to contraction of the ventricles of heart 11. Accelerometer 24 may generate the acceleration signal while it is positioned on a chest wall of the patient 12 (external to patient 12 and not implanted in patient 12).

In some examples, processor 30 receives, from accelerometer 24, an acceleration signal indicating acceleration in a single axis, such as an axis that is aligned with an anteroposterior direction of patient 12. This single axis acceleration may be generated by a single axis accelerometer. In other examples, processor 30 receives, from accelerometer 24, an acceleration signal indicating acceleration in multiple axes, and processor 30 may determine the cardiac dyssynchrony status of patient 12 based on movement of a chest wall of patient 12 in only one direction.

Determining a cardiac dyssynchrony status of patient 12 based on movement of a chest wall of patient 12 in only one direction, e.g., in only the anteroposterior direction, may help simplify the computation required, by processor 30, to determine the cardiac dyssynchrony status. In addition, in some cases, determining a cardiac dyssynchrony status of patient 12 based on movement of a chest wall of patient 12 in only one direction may help reduce or eliminate noise attributable to chest wall motion from other sources, such as respiratory activity of patient 12. In other examples, however, processor 30 may receive an acceleration signal (e.g., three signals) indicative of motion of chest wall 26 in multiple directions.

Processor 30 may receive the ECG (50) and accelerometer signal (52) at different time or contemporaneously. However, the received ECG and accelerometer signal completely or at least partially overlap in time, such that the ECG and accelerometer signal may represent patient parameters that occurred at the same time.

Processor 30 integrates the received accelerometer signal, thereby generating a velocity signal that is indicative of the velocity of chest wall 26 that is at least partially caused by contraction of the ventricles of heart 11 (54). That is, the derivative of the velocity signal with respect to time is the acceleration signal with respect to time. In some examples, processor 30 integrates the received accelerometer signal (54) in response to receiving the accelerometer signal or in response to another control, such as a predetermined schedule stored by memory 34 (FIG. 2).

In some examples, processor 30 may execute signal processing software stored by memory 34 in order to derive a function that is the integral of the received accelerometer signal. In some examples, if processor 30 receives an accelerometer signal with multiple portions (e.g., two or three), each indicating acceleration in a respective multiple axis, processor 30 may integrate each of the portions to generate the velocity signals indicative of the velocity components of each of the portions. In other examples in which processor 30 receives an accelerometer signal with multiple portions (e.g., two or three), each indicating acceleration in a respective multiple axis, processor 30 may integrate only one of the portions, e.g., the portion corresponding to the anteroposterior direction to generate the velocity signals indicative of the velocity in the anteroposterior direction.

In some examples, processor 30 processes the accelerometer signal prior to integrating the signal. For example, processor 30 may apply a low pass filter to the signal in order to filter out noise (e.g., attributable to chest wall 26 motion from respiratory activity of patient 12). In one example, the low pass filter has a cutoff frequency of about 20 Hz to about 50 Hz. In addition, or instead of the low pass filter, processor 30 may normalize the accelerometer signal. For example, processor 30 may normalize the accelerometer signal by dividing the signal amplitude by a maximum absolute amplitude value within a particular time range.

In order to reduce the computational complexity of the integration, rather than integrating the entire received accelerometer signal, processor 30 may select and integrate a segment of the accelerometer signal that is between two predetermined points in time, which may be selected such that at last one cardiac cycle (e.g., a heartbeat) occurs contemporaneously with the segment of the accelerometer signal. Thus, the segment of the accelerometer signal that is integrated is the approximately same duration or longer than a cardiac cycle of heart 11 of patient 12, such as a duration of about 200 ms to about 600 ms, or a duration of about 400 ms. For example, processor 30 may integrate a segment of the accelerometer signal that corresponds in time to a segment of the temporally corresponding electrical cardiac signal starting at a Q wave or R-wave and extending about 400 ms (or another duration of time). In these examples, processor 30 determines the definite integral of the accelerometer signal. In other examples, processor 30 may integrate the entire received accelerometer signal, which, if continuously received from accelerometer 24, may be an indefinite integral.

After generating the velocity signal (54) based on the acceleration signal generated by accelerometer 24, processor 30 temporally correlates the ECG signal and the velocity signal (56). For example, processor 30 may temporally correlate the ECG signal and the velocity signal in response to the integration of the accelerometer signal. In one example, in order to temporally correlate the signals, processor 30 determines the portion of the ECG signal that occurred when a particular portion of the velocity signal was sensed by accelerometer 24. In this way, processor 30 may determine the electrical cardiac activity of patient observed when a particular velocity of chest wall 26 of patient 12 was observed. In some examples, processor 30 generates and presents, via a display of user interface 36 of diagnostic device 14 (FIG. 2), a graphical display of the overlapping ECG and velocity signals, where the signals are matched up by time (e.g., a display similar to the graphs shown in FIGS. 4A and 4B). In these examples, a clinician may view the display and relatively quickly ascertain the ECG signal sensed by sensing module 32 while a certain velocity of chest wall 26 was sensed by accelerometer 24. The visual display of the temporally correlated ECG and velocity signals may be useful for determining whether patient 12 exhibits ventricular dyssynchrony.

However, in some cases, a clinician may not be able to determine the patient's cardiac dyssynchrony status based merely on a visual representation of the temporally correlated ECG and velocity signals. Diagnostic device 14 is configured to provide an output indicative of a cardiac dyssynchrony status, which provides a quantitative, qualitative, or both quantitative and qualitative metric of the extent of the patient's ventricular dyssynchrony.

In accordance with the technique shown in FIG. 3, processor 30 determines (e.g., computes) a time delay between a greatest peak of the velocity signal and a preceding deflection of the ECG signal that is indicative of the ventricular electrical activation of heart 11 (58). Processor 30 may determine the time delay automatically, without user input that provides the time delay. For example, processor 30 may determine the time delay immediately after temporally correlating of the ECG and velocity signal and in response to the temporal correlation.

In the example technique shown in FIG. 3, the deflection of the ECG signal that is indicative of the ventricular electrical activation is selected to be a Q-wave of the ECG signal. A QRS complex of the ECG signal corresponds to the depolarization of the right and left ventricles of heart 11 of patient 12. The Q-wave is a downward deflection of the ECG after a P-wave, which may indicate atrial depolarization. A Q-wave may be selected as the deflection from which the time delay is determined if, for example, the cardiac rhythm management stimulation is delivered to heart 11. In other examples, the deflection of the ECG signal that is indicative of the ventricular electrical activation is selected to be an R-wave or an S-wave of the ECG signal. An R-wave may be selected as the deflection from which the time delay is determined if, for example, the intrinsic cardiac activity of patient 12 is sensed and no cardiac rhythm management stimulation is provided to heart 11.

In some examples, the time delay determined by processor 30 (58) may be based on a plurality of cardiac cycles (heartbeats), such as two or more cardiac cycles, such as two to about 32 cardiac cycles. For example, processor 30 may determine a first time delay for a first Q-wave and a subsequent greatest velocity peak occurring after the first Q-wave and prior to a subsequent P-wave (which may indicate the occurrence of another cardiac cycle), a second time delay for a second Q-wave and a respective subsequent greatest velocity peak occurring after the second Q-wave and prior to a subsequent P-wave, and a third time delay for a third Q-wave and a respective subsequent greatest velocity peak occurring after the third Q-wave and prior to a subsequent P-wave. In some examples, the first, second, and third Q-waves occur sequentially. In some cases, the first, second, and third Q-waves are non-sequential and may be separated by one or more cardiac cycles. In some examples, processor 30 may then determine the time delay based on an average of the first, second, and third time delays, or determine the time delay based on the lowest or highest time delay in the subset. Processor 30 may be configured to implement to one or more of these time delay determination algorithms.

Using multiple cardiac cycles to determine the time delay that may be indicative of the extent (e.g., severity) of the cardiac dyssynchrony of a patient may, in some cases, provide a more accurate indication of the cardiac dyssynchrony status of the patient. For example, assessing the extent of a patient's cardiac dyssynchrony based on an average time delay that is based on multiple cardiac cycles may reduce the possibility that the assessment will be based on an outlier time delay (e.g., an unusually long or short time delay for patient 12) that may not accurately represent the patient's cardiac dyssynchrony status. Other techniques for reducing the possibility that the cardiac dyssynchrony assessment by processor 30 will be based on an outlier time delay may be used instead of or in addition to using multiple cardiac cycles.

Because the ventricular dyssynchrony may be characterized by late left ventricular contraction relative to the electrical activation of the right ventricle, the time delay between the electrical activation of the right ventricle (e.g., the Q-wave) and the greatest peak of the velocity signal may be used as a numerical metric that indicates the extent of the dyssynchrony. The determined time delay may indicate the delay between the time the left ventricle of heart 11 should have contracted, e.g., in a healthy patient with ventricular synchrony (wherein the ventricles contract in synchrony or nearly in synchrony with little to no delay), and the actual time of the left ventricular contraction of patient 12.

The time delay may be a quantitative metric indicative of the extent of the patient's ventricular dyssynchrony. A numerical metric may be useful for evaluating the cardiac dyssynchrony of patient 12 because it provides a clinician with a relatively consistent way of comparing patient 12 to a healthy patient without ventricular dyssynchrony, and a way of determining the severity of the dyssynchrony. With some patients, the longer the determined time delay, the more severe the dyssynchrony.

In the technique shown in FIG. 3, processor 30 generates an output indicative of the cardiac dyssynchrony status of the patient, which is determined based on the determined time delay (60). Processor 30 may, for example, generate the output indicative of the cardiac dyssynchrony status of the patient in response to determining the time delay (58). In one example, the output is a flag, signal, or other electronic indication of the cardiac dyssynchrony status, which processor 30 stores in memory 34 or a memory of another device, such as a remote database. In another example, processor 30 provides the output via user interface 36. For example, processor 30 may present, via a display of user interface 36 of diagnostic device 14, a visual indication of the determine time delay. As an example, if the determined time delay is 0.2 milliseconds, processor 30 may generate a display that indicates, to a user, the time delay between the Q-wave (or other deflection of the ECG signal indicative of ventricular electrical activation) and the greatest peak of the velocity signal was 0.2 milliseconds. The time delay may be displayed along with a graphical representation of the temporally correlated electrical cardiac signal and velocity signal, examples of which are shown in FIGS. 4A and 4B and described below.

In addition, or instead, of the visual indication of the determine time delay, processor 30 may present, via the display of user interface 36 of diagnostic device 14, an indication of the relative severity or other category of the cardiac dyssynchrony of patient 12. Processor 30 may determine the relative severity or other category of the cardiac dyssynchrony status of patient 12 based on the determined time delay. An example technique for determining a category of the cardiac dyssynchrony of patient 12 is described with respect to FIG. 5. The category of the cardiac dyssynchrony may be a qualitative metric generated by processor 30 that is indicative of the extent of the patient's ventricular dyssynchrony.

The determined time delay and/or relative severity or other category of the cardiac dyssynchrony status of patient 12 may be presented as an alphanumeric display, graphical display (e.g., different symbols may represent the dyssynchrony status), color coded display (e.g., different colors may represent different severity levels of the dyssynchrony status), or any other suitable display.

In other examples, instead of or in addition to presenting information via a display of user interface 36 of diagnostic device 14, processor 30 may control a printer to output a printed (e.g., on a piece of paper) indication of the cardiac dyssynchrony status of the patient, including any of the indications discussed above. Other mechanisms by which processor 30 may generate an output indicative of the cardiac dyssynchrony status of patient 12 may also be used in addition to or instead of the mechanisms described above. For example, processor 30 may control an audio output mechanism of user interface 36 to generate an audible indication of the cardiac dyssynchrony status of patient 12, such as an automated audible recitation of the time delay, a predetermined sound associated with the time delay or having a duration associated with the time delay, or a determined other category of the cardiac dyssynchrony status of patient 12. As another example, processor 30 may control a somatosensory output mechanism of user interface 36 to generate a somatosensory indication (e.g., a vibration) of the cardiac dyssynchrony status of patient 12, such as a particular vibration pattern or duration associated with the time delay.

FIG. 4A is a conceptual graphical representation of an example ECG signal 62 of a patient that does not exhibit ventricular dyssynchrony or at least ventricular dyssynchrony that does not merit CRT, and an example velocity signal 64. ECG signal 62 is a conceptual illustration of an ECG signal that may be generated by a device, whether implanted or external to the patient, and represents electrical cardiac activity of a patient that does not have ventricular dyssynchrony. Velocity signal 64 is a conceptual illustration of a velocity signal that may be generated by integrating an accelerometer signal sensed via an external accelerometer placed on a chest wall of the patient. The data shown in FIG. 4A was not generated from a patient, but was graphically generated for purposes of illustrating what example electrical cardiac signals and velocity signals generated from a patient may look. The graphical representation shown in FIG. 4A is only one example of temporally correlated ECG and velocity signals, and other patients that do not exhibit ventricular dyssynchrony or at least ventricular dyssynchrony that does not merit CRT may have other signal morphologies.

ECG signal 62 and velocity signal 64 are temporally correlated, and displayed in an overlaid manner, such that the ECG signal of a heartbeat and the corresponding velocity of the chest wall of the patient is shown. As shown in FIG. 4A, in some patients, synchronous ventricular contraction may result in one peak 68 of velocity signal 64 following Q-wave 66 of ECG signal 62. As the left and right ventricles of the patient contract in synchrony, the chest wall of the patient (on which the accelerometer is placed), moves over time in one continuous motion, which presents as one peak of velocity signal 64. In the patient with no ventricular dyssynchrony, during one cardiac cycle, there is some time delay $T_1$ between Q-wave 66 of ECG signal 62 and a subsequent greatest peak 68 of velocity signal 64, which may be attributable to the time required for depolarization of the patient's heart to cause the ventricular contraction.

It can be desirable to minimize the time delay $T_1$ between the electrical activation of the ventricles and the mechanical contraction of both ventricles, which is indicated by peak 68 of velocity signal 64. In some patients that do not exhibit ventricular dyssynchrony, the average time delay $T_1$ may be about 30 ms to about 100 ms.

FIG. 4B is a conceptual graphical representation of an example ECG signal 70 of a patient that has ventricular dyssynchrony, and an example velocity signal 72. ECG signal 70 is a conceptual illustration of an ECG signal that may be generated by a device, whether implanted or external to the patient, and represents electrical cardiac activity of a patient that exhibits ventricular dyssynchrony and velocity signal 72 is a conceptual illustration of a velocity signal that may be generated by integrating an accelerometer signal sensed via an external accelerometer placed on a chest wall of the patient proximate to a heart of the patient. As with FIG. 4A, the data shown in FIG. 4B was not generated from a patient, but was graphically generated for purposes of illustrating what example electrical cardiac signals and velocity signals generated from a patient may look like. The graphical representation shown in FIG. 4B is only one example of temporally correlated ECG and velocity signals, and other patients that exhibit ventricular dyssynchrony may have other signal morphologies.

ECG signal 70 and velocity signal 72 are temporally correlated, and displayed in an overlaid manner in FIG. 4B. In some patients with ventricular dyssynchrony, during one cardiac cycle, there may be a time delay $T_2$ between Q-wave 74 of ECG signal 70 and a subsequent greatest peak 76 of velocity signal 72, where time delay $T_2$ is greater than the time delay $T_1$ observed in the patient without ventricular dyssynchrony.

As shown in FIG. 4B, asynchronous contraction of one ventricle relative to the other may result in multiple peaks 76, 78, 80 of velocity signal 72 following Q-wave 74 of ECG signal 74. Each velocity peak 76, 78, 80 may indicate, for example, the movement of the chest wall of the patient as each ventricle or part of a ventricle contracts. The contraction of the later-contracting ventricle, which indicates the dyssynchrony between the ventricles of the patient's heart, is indicated by greatest peak 76 in velocity signal 72 because, at least in some patients, the greatest velocity peak may coincide with when the time when electrical activity has propagated through heart 11, i.e., when heart 11 has depolarized.

Time delay $T_2$ may be used as a metric to indicate the extent of the ventricular dyssynchrony, whether interventricular or intraventricular, of the patient. The magnitude of the time delay $T_2$ may indicate the degree of ventricular dyssynchrony. For example, a relatively small time delay $T_2$ (e.g., as indicated by comparison to a threshold value) may indicate a less severe cardiac dyssynchrony status of the patient compared to a relatively large time delay $T_2$ (e.g., as indicated by comparison to the threshold value).

FIG. 5 is a flow diagram of an example technique by which processor 30 of diagnostic device 14 can determine a cardiac dyssynchrony status of patient 12 based on time delay $T_2$. In the example shown in FIG. 5, the cardiac dyssynchrony status of patient 12 includes a category of time delay $T_2$ between a Q-wave (or other deflection of the ECG signal indicative of ventricular electrical activation) and a subsequent greatest peak of the velocity signal determined based on an acceleration signal generated by accelerometer 24.

In accordance with the technique shown in FIG. 5, processor 30 determines time delay $T_2$ (90) e.g., using the technique shown in FIG. 3, retrieving a stored time delay $T_2$, which was previously determined, from memory 34 (FIG. 2), or receiving the time delay $T_2$ from another device, such as a remote database that stores patient data or another diagnostic device that determined the time delay. Processor 30 compares the time delay $T_2$ to a first threshold value and determines whether the time delay is less than the first threshold value (92). The first threshold value may be stored by memory 34 of diagnostic device 14 (FIG. 2) or another device, such as a remote database, a diagnostic device, an external or implantable cardiac stimulator, or another medical device.

The first threshold value may indicate the time delay that is indicative of dyssynchrony of patient 12 or a severity of dyssynchrony that may require cardiac rhythm management therapy, e.g., via an implanted or external device that delivers electrical stimulation to heart 11. Accordingly, in response to determining the time delay $T_2$ is less than the first threshold value, processor 30 determines patient 12 does not have dyssynchrony or at least dyssynchrony that merits cardiac rhythm management therapy and generates a first category indication (94). Processor 30 may, for example, generate the first category indication in response to determining the time delay $T_2$ is less than the first threshold value.

In some examples, each category indication described herein may be a type of output generated by processor 30 and presented to a user of diagnostic device 14 via user interface 36 of device 14 (FIG. 2). As described above with respect to FIG. 3, the output can be, for example, a graphical, alphanumeric, audible, somatosensory or other indication of the determined category indication. In addition to, or instead of, generating an output indicative of the category indication, each category indication described herein may be associated with patient 12 and stored by processor 30 in memory 34 of diagnostic device 14 or a memory of another device (e.g., a remote database or a cardiac stimulator). The category indication associated with patient 12 may be later retrieved by a clinician for, e.g., diagnosis of patient 12 or therapy regimen selection.

In some examples, processor 30 generates only two category indications, a first indicating patient 12 does not exhibit cardiac dyssynchrony or cardiac dyssynchrony that merits cardiac rhythm management therapy and a second indicating patient 12 exhibits cardiac dyssynchrony or cardiac dyssynchrony that merits cardiac rhythm management therapy. In the example shown in FIG. 5, in response to determining the time delay $T_2$ is not less than (e.g., is greater than or equal to) the first threshold value (92), processor 30 determines that heart 11 of patient 12 exhibits dyssynchrony that merits cardiac rhythm management therapy or at least further evaluation to determine whether such therapy is desirable. Processor 30 may then generate a second category indication (different from the first category indication) that indicates the dyssynchrony of patient 12 falls into such category (98).

In the example shown in FIG. 5, processor 30 generates more than two category indications. Thus, in accordance with the technique shown in FIG. 5, in response to determining that the time delay $T_2$ is indicative of cardiac dyssynchrony or dyssynchrony that may merit cardiac rhythm management therapy, processor 30 further categorizes the dyssynchrony of patient 12. In some examples, each of the plurality of categories from which processor 30 selects a category of the dyssynchrony of patient 12 may also be associated with a severity indication and/or a recommended type of cardiac rhythm management therapy. Different types of cardiac rhythm management therapy may include, for example, biventricular pacing, right ventricular pacing, and left ventricular pacing. In this manner, processor 30 may automatically recommend a type of cardiac rhythm management therapy for patient 12 based on the determined time delay $T_2$. For example, processor 30 may reference a data structure stored by memory 34 of diagnostic device 14 or another device that associates one or more ranges of time delays with types of cardiac rhythm management therapy.

In accordance with the example technique shown in FIG. 5, after determining the time delay $T_2$ is not less than the first threshold value (92), processor determines whether the time delay $T_2$ is less than a second threshold value, which is greater than the first threshold value (96). In response to determining the time delay $T_2$ is less than the second threshold value, processor 30 determines that the cardiac dyssynchrony of patient 12 falls into a second category and generates a second category indication (98). The second category indication may indicate a more serious ventricular dyssynchrony state than the ventricular dyssynchrony state associated with the first category indication. Processor 30 may, for example, generate the second category indication in response to determining the time delay $T_2$ is less than the second threshold value.

On the other hand, in response to determining that the time delay $T_2$ is not less than the second threshold value (96), processor 30 determines the cardiac dyssynchrony of patient 12 falls into a third category and generates a third category indication (100). The third category indication may indicate a more serious ventricular dyssynchrony than the dyssynchrony states associated with the first and second category indications. Processor 30 may, for example, generate the third category indication in response to determining the time delay $T_2$ is not less than the first threshold value.

In the technique shown in FIG. 5, the threshold values may also define different time ranges. For example, a first time range may be from zero to just less than the first threshold value (e.g., within 0.1 to about 0.001 milliseconds of the first threshold value), a second time range may be from the first threshold value to just less than the second threshold value (e.g., within 0.1 to about 0.001 milliseconds of the second threshold value), and a third time range may be from the second threshold value to the third threshold value. Thus, processor 30 may determine whether the determine time delay falls within the first, second, or third time ranges in order to generate a category indication that is indicative of the cardiac dyssynchrony status of the patient.

When the threshold values described with respect to FIG. 5 are associated with a recommended type of cardiac rhythm management therapy, the thresholds may be determined to be, for example, thresholds that indicate patient 12 may respond positively to the associated type of therapy. A positive response may be, for example, a decrease in the time delay $T_2$ upon delivery of the cardiac rhythm management therapy by a medical device, thereby decreasing the amount of interventricular or intraventricular dyssynchrony. The thresholds may be selected based on historical data from a plurality of patients and/or test data (e.g., from computer generated modeling).

In one example, the second category indication shown in FIG. 5 is associated with right ventricular pacing and/or left ventricular pacing, and the third category indication is associated with biventricular pacing. Thus, if processor 30 generates a second category indication (98), the cardiac dyssynchrony status provided by processor 30 may include a recommendation to the clinician to trial right ventricular pacing and/or left ventricular pacing on patient 12. On the other hand, if processor 30 generates a third category indication (100), the cardiac dyssynchrony status provided by processor 30 may include a recommendation to the clinician to trial biventricular pacing on patient 12. In other examples, processor 30 may generate one of four category indications, where a first category indicates no therapy is recommended for patient 12, the second category indicates right ventricular pacing is recommended for patient 12, the third category indicates left ventricular pacing is recommended for patient 12, and the fourth category indicates biventricular pacing is recommended for patient. However, in other examples, other combinations and orders of category indications and associated therapy recommendations may also be used.

After delivery of cardiac rhythm management therapy to heart 11 of patient 12 by a medical device (e.g., CRT delivered by an implanted medical device), a clinician may use diagnostic device 14 to determine whether the cardiac dyssynchrony has improved or whether one or more therapy delivery parameters (e.g., timing between pacing pulses) of the medical device may need to be adjusted to provide more efficacious cardiac therapy to patient 12. Diagnostic device 14 may, e.g., by implementing the technique shown in FIG. 3, determine the time delay between a deflection in an electrical cardiac signal indicative of electrical ventricular activation and a subsequent peak in a velocity signal determined based on a signal generated by accelerometer 24. In some examples, the time delay is determined while therapy delivery by the medical device is suspended, e.g., if the clinician wants to determine whether the cardiac therapy has improved the cardiac dyssynchrony of the patient's intrinsic cardiac cycle. In other examples, the time delay is determined while the medical device is delivering therapy, e.g., if the clinician wants to determine if one or more therapy parameters of the medical device may need to be adjusted.

Processor 30 of diagnostic device 14 may determine, based on the determined time delay, the cardiac dyssynchrony status of patient 12 and control user interface 36 (FIG. 2) to generate an output indicative of the cardiac dyssynchrony status. The clinician may consider this output and subsequently take a suitable action, such as adjusting the therapy regimen of patient 12 (e.g., suspending delivery of therapy until cardiac dyssynchrony is observed again or adjusting one or more therapy delivery parameters of the medical device).

In some examples, processor 30 is configured to generate an output via user interface 36 (FIG. 2) that recommends a course of action for adjusting the cardiac rhythm therapy. For example, if biventricular pacing is delivered to patient 12 and processor 30 detects a time delay between a deflection in a Q-wave sensed while the device is delivering the biventricular pacing and a subsequent peak in a velocity signal determined based on a signal generated by accelerometer 24 that is greater than a predetermined threshold value, processor 30 may recommend decreasing the biventricular pacing interval such that the left ventricle is paced closer in time to the right ventricle to reduce a delay in left ventricular contraction relative to right ventricular contraction. Processor 30 may, for example, control user interface 36 to generate any suitable visual, audible, or somatosensory output that indicate the recommended course of action for adjusting the cardiac rhythm therapy delivered to patient 12.

While examples in which the left ventricle is the later contracting ventricle, in other examples, the techniques, devices, and systems of this disclosure may be used to assess cardiac dyssynchrony for patients in which the right ventricle is the later contracting ventricle.

The techniques described in this disclosure, including those attributed to diagnostic device 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in diagnostic devices, programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by processor 30 of device 14, any one or more parts of the techniques described herein may be implemented by a processor of diagnostic device 14 or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A system comprising:
   an external accelerometer configured to generate an acceleration signal indicative of chest wall motion of a patient; and
   a processor configured to integrate the acceleration signal to generate a velocity signal, receive an electrical cardiac signal indicative of electrical cardiac activity of the patient, temporally correlate the velocity signal with the electrical cardiac signal, determine a time delay between a deflection of the electrical cardiac signal indicative of electrical activation of a ventricle of a heart of the patient and a subsequent greatest peak of the velocity signal, and generate an output indicative of a cardiac dyssynchrony status of the patient based on the time delay.

2. The system of claim 1, wherein the electrical cardiac signal comprises at least one of an electrocardiogram or an electrogram, and the deflection is a Q-wave.

3. The system of claim 1, wherein the electrical cardiac signal comprises at least one of an electrocardiogram or an electrogram, and the deflection is an R-wave.

4. The system of claim 1, wherein the accelerometer is configured to generate an acceleration signal indicative of movement of the chest wall of the patient in a single axis.

5. The system of claim 1, further comprising a user interface, wherein the processor is configured to generate the output indicative of the cardiac dyssynchrony status of the patient by at least controlling the user interface to display a visible indication of the time delay.

6. The system of claim 1, further comprising a user interface, wherein the processor is configured to generate the output indicative of the cardiac dyssynchrony status of the patient by at least controlling the user interface to generate an audible or somatosensory indication of the time delay.

7. The system of claim 1, further comprising a memory, wherein the processor stores the output indicative of the cardiac dyssynchrony status in the memory.

8. The system of claim 1, wherein the processor is configured to determine the cardiac dyssynchrony status by at least comparing the time delay to a threshold value, and wherein the processor is configured to determine a first cardiac dyssynchrony status and generate a first output indicative of the first cardiac dyssynchrony status in response to determining the time delay is less than the threshold value, and determine a second cardiac dyssynchrony status and generate a second output indicative of the second cardiac dyssynchrony status in response to determining the time delay is not less than the threshold value.

9. The system of claim 1, wherein the processor is configured to generate the output by at least automatically generating an output recommending a type of cardiac rhythm management therapy based on the time delay.

10. The system of claim 9, wherein the processor is configured to determine the type of cardiac rhythm management therapy by at least comparing the time delay to a plurality of time delay ranges associated with respective types of cardiac rhythm management therapy, determining which time delay range of the plurality of time delay ranges the time delay falls into, and selecting the cardiac rhythm management therapy associated with the determined time delay range.

11. The system of claim 1, further comprising a sensing module configured to generate the electrical cardiac signal.

12. The system of claim 1, wherein the processor is configured to determine the time delay by at least quantifying the time delay.

13. The system of claim 1, wherein the processor is configured to compare the time delay to a threshold value, and generate the output indicative of the cardiac dyssynchrony status of the patient based on the comparison.

14. A method comprising:
with a processor, receiving, from an external accelerometer, an acceleration signal indicative of chest wall motion of the patient, wherein the external accelerometer generates the acceleration signal while the external accelerometer is positioned on a chest wall of a patient;
with the processor, integrating the acceleration signal to generate a velocity signal;
with the processor, receiving an electrical cardiac signal of a patient indicative of electrical cardiac activity of the patient;
with the processor, temporally correlating the velocity signal with the electrical cardiac signal;
determining a time delay between a deflection of the electrical cardiac signal indicative of electrical activation of a ventricle of a heart of the patient and a subsequent greatest peak of the velocity signal; and
generating an output indicative of a cardiac dyssynchrony status of the patient based on the time delay.

15. The method of claim 14, wherein the electrical cardiac signal comprises at least one of an electrocardiogram or an electrogram, and the deflection of the electrical cardiac signal is a Q-wave of the at least one of the electrocardiogram or the electrogram.

16. The method of claim 14, wherein the electrical cardiac signal comprises at least one of an electrocardiogram or an electrogram, and the deflection of the electrical cardiac signal is an R-wave of the at least one of the electrocardiogram or the electrogram.

17. The method of claim 14, wherein generating the acceleration signal indicative of chest wall motion of the patient comprises generating the acceleration signal indicative of movement of the chest wall of the patient in a single anteroposterior axis.

18. The method of claim 14, wherein generating the output indicative of the cardiac dyssynchrony status of the patient comprises controlling a user interface of a computing device to display a visible indication of the time delay.

19. The method of claim 14, wherein generating the output indicative of the cardiac dyssynchrony status of the patient comprises controlling a user interface of a computing device to generate an audible or somatosensory indication of the time delay.

20. The method of claim 14, further comprising determining, with the processor, the cardiac dyssynchrony status, wherein determining the cardiac dyssynchrony status comprises:
with the processor, comparing the time delay to a threshold value;
with the processor, determining a first cardiac dyssynchrony status and generating a first output indicative of the first cardiac dyssynchrony status in response to determining the time delay is less than the threshold value; and
with the processor, determining a second cardiac dyssynchrony status and generating a second output indicative of the second cardiac dyssynchrony status in response to determining the time delay is not less than the threshold value.

21. The method of claim 14, wherein generating the output comprises, with the processor, automatically generating an output recommending a type of cardiac rhythm management therapy based on the time delay.

22. The method of claim 21, further comprising determining the type of cardiac rhythm management therapy based on the time delay, wherein determining the type of cardiac rhythm management therapy comprises, with the processor:
comparing the time delay to a plurality of time delay ranges associated with respective types of cardiac rhythm management therapy;
determining which time delay range of the plurality of time delay ranges the time delay falls into, and
selecting the cardiac rhythm management therapy associated with the determined time delay range.

23. The method of claim 14, further comprising:
with a sensing module, generating the electrical cardiac signal of a patient indicative of electrical cardiac activity of the patient; and
transmitting the signal to the processor.

24. The method of claim 14, wherein determining the time delay comprises quantifying the time delay.

25. The method of claim 14, further comprising, with the processor, comparing the time delay to a threshold value, wherein generating the output indicative of the cardiac dyssynchrony status of the patient comprises generating the output based on the comparison.

26. A system comprising:
means for generating an acceleration signal indicative of chest wall motion of a patient from a location external to the patient;
means for integrating the acceleration signal to generate a velocity signal;
means for temporally correlating the velocity signal with an electrical cardiac signal indicative of electrical cardiac activity of the patient;
means for determining a time delay between a deflection of the electrical cardiac signal indicative of electrical activation of a ventricle of a heart of the patient and a subsequent greatest peak of the velocity signal; and
means for generating an output indicative of a cardiac dyssynchrony status of the patient based on the time delay.

27. The system of claim 26, wherein the means for generating an acceleration signal is configured to generate an acceleration signal indicative of movement of the chest wall of the patient in a single axis.

28. The system of claim 26, further comprising means for determining the cardiac dyssynchrony status that is configured to determine the cardiac dyssynchrony status by at least comparing the time delay to a threshold value, determining a first cardiac dyssynchrony status and generating a first output indicative of the first cardiac dyssynchrony status in response to determining the time delay is less than the threshold value, and determining a second cardiac dyssynchrony status and generating a second output indicative of the second cardiac dyssynchrony status in response to determining the time delay is not less than the threshold value.

29. The system of claim 26, wherein the means for generating the output is configured to automatically generate the output recommending a type of cardiac rhythm management therapy based on the time delay.

30. A non-transitory computer-readable medium comprising instructions that, when executed by a processor, cause the processor to:
receive, from an external accelerometer, an acceleration signal indicative of chest wall motion of the patient, wherein the external accelerometer generates the acceleration signal while the external accelerometer was positioned on a chest wall of a patient;
integrate the acceleration signal to generate a velocity signal;
receive an electrical cardiac signal of a patient indicative of electrical cardiac activity of the patient;
temporally correlate the velocity signal with the electrical cardiac signal;
determine a time delay between a deflection of the electrical cardiac signal indicative of electrical activation of a ventricle of a heart of the patient and a subsequent greatest peak of the velocity signal; and
generate an output indicative of a cardiac dyssynchrony status of the patient based on the time delay.

* * * * *